United States Patent
Lee et al.

(10) Patent No.: US 9,220,757 B2
(45) Date of Patent: Dec. 29, 2015

(54) METHOD FOR INDUCING IN VIVO MIGRATION OF STEM CELL

(75) Inventors: Jin Woo Lee, Goyang-si (KR); Min Sung Park, Seoul (KR); Yun Hee Kim, Seoul (KR)

(73) Assignee: Tego Science Inc., Seoul (KR)

( * ) Notice: Subject to any disclaimer, the term of this patent is extended or adjusted under 35 U.S.C. 154(b) by 0 days.

(21) Appl. No.: 14/003,364

(22) PCT Filed: Jan. 26, 2012

(86) PCT No.: PCT/KR2012/000618
§ 371 (c)(1),
(2), (4) Date: Sep. 5, 2013

(87) PCT Pub. No.: WO2012/121485
PCT Pub. Date: Sep. 13, 2012

(65) Prior Publication Data
US 2013/0344119 A1     Dec. 26, 2013

(30) Foreign Application Priority Data

Mar. 8, 2011 (KR) .................. 10-2011-0020221
Jan. 5, 2012 (KR) .................. 10-2012-0001563

(51) Int. Cl.
| | |
|---|---|
| *A61L 27/54* | (2006.01) |
| *A61L 27/18* | (2006.01) |
| *A61K 38/19* | (2006.01) |
| *A61K 38/20* | (2006.01) |
| *A61L 27/56* | (2006.01) |
| *A61L 27/58* | (2006.01) |
| *C07K 14/52* | (2006.01) |
| *C07K 14/54* | (2006.01) |
| *C07K 17/02* | (2006.01) |

(52) U.S. Cl.
CPC ........... *A61K 38/2053* (2013.01); *A61K 38/195* (2013.01); *A61L 27/54* (2013.01); *A61L 27/56* (2013.01); *A61L 27/58* (2013.01); *C07K 14/523* (2013.01); *C07K 14/5421* (2013.01); *C07K 17/02* (2013.01); *A61L 2300/252* (2013.01); *A61L 2300/412* (2013.01); *A61L 2430/24* (2013.01)

(58) Field of Classification Search
CPC . A61K 38/195; A61K 38/20; A61K 38/2053; A61L 300/252; A61L 2300/412; A61L 2430/24; A61L 27/54; A61L 27/56; A61L 27/05; C07K 14/523; C07K 14/5421; C07K 17/02
See application file for complete search history.

(56) References Cited

U.S. PATENT DOCUMENTS

| | | | | |
|---|---|---|---|---|
| 5,504,003 | A * | 4/1996 | Li et al. ..................... | 435/365.1 |
| 2008/0213389 | A1 * | 9/2008 | Lelkes et al. ................ | 424/572 |

FOREIGN PATENT DOCUMENTS

WO    WO-2008-088381 A2    7/2008

OTHER PUBLICATIONS

Inokuma et al., "CTACK/CCL27 accelerates skin regeneration via accumulation of bone marrow-derived keratinocytes," Stem Cells. 24(12):2810-6 (2006).
Ringe et al., "Towards in situ tissue repair: human mesenchymal stem cells express chemokine receptors CXCR1, CXCR2 and CCR2, and migrate upon stimulation with CXCL8 but not CCL2" J Cell Biochem. 101(1):135-46 (2007).
Sordi et al., "Bone marrow mesenchymal stem cells express a restricted set of functionally active chemokine receptors capable of promoting migration to pancreatic islets," Blood. 106(2):419-27 (2005).
International Search Report for International Application No. PCT/KR2012/000618, mailed Sep. 26, 2012 (3 pages).

* cited by examiner

*Primary Examiner* — Abigail Fisher
(74) *Attorney, Agent, or Firm* — Clark & Elbing LLP; Susan M. Michaud (57) ABSTRACT

The present invention relates to an implantable composition for treating a damaged tissue and a method for inducing an in vivo migration of a cell for treatment to a damaged tissue region. The present invention treats the damaged tissue by inducing/promoting homing of a cell for tissue generation by implanting a biodegradable scaffold reacted with chemotactic factors (for example, IL-8 or MIP-3α) to a damaged location (for example, joint cartilage or skin). Thus, the composition of the present invention can not only be applied to the treatment of a damaged bone tissue, a joint cartilage, or a skin tissue more conveniently and efficiently compared to the conventional technology, but can also be used as a useful treatment supplement agent in cell treatment using allogeneic cell by enabling efficient utilization of cell resources for treatment, the cell resources which are high in scarcity.

14 Claims, 11 Drawing Sheets

METHOD FOR INDUCING IN VIVO MIGRATION OF STEM CELL

CROSS-REFERENCE TO RELATED APPLICATIONS

This application is the U.S. national stage filing under 35 U.S.C. §371 of international application PCT/KR2012/000618, filed Jan. 26, 2012, which claims priority from Korean Patent Applications 10-2011-0020221, filed Mar. 8, 2011 and 10-2012-0001563, filed Jan. 5, 2012.

FIELD OF THE INVENTION

The present invention relates to an implantable composition for treating a damaged tissue and a method for inducing an in vivo migration of a cell for treatment to a damaged tissue region.

DESCRIPTION OF THE RELATED ART

Stem cells are cells that can differentiate into various cell types constituting the tissues of an organism, and collectively refer to the cells in an undifferentiated state that can be obtained from embryonic, fetal and adult tissues. The stem cells differentiate into specific cell types under necessary stimulation (environment). Unlike the differentiated cells whose cell division has stopped, they can produce the cells identical to themselves through cell division (self-renewal) and can proliferate (expansion). Also, they can differentiate into other cells under different environment or stimulation (plasticity).

An articular cartilage is an avascular tissue consisting mainly of proteoglycan and type II collagen, and includes about 5% of cartilage cells in the tissue volume [1]. Once articular cartilages are destroyed, chondrocytes do not nearly migrate to the injury region and the injured articular cartilages do not recover spontaneously [2]. Representative biological methods for treating the injured articular cartilage are subchondral drilling and autologous chondrocyte transplantation. Autologous chondrocytes transplantation is a promising method to treat articular cartilage injuries by transplanting autologous chondrocytes to the injury region. However, there are disadvantages that the surgery is repeatedly required and donors are limited. Subchondral drilling is a method to treat articular cartilage injuries using introducing bone marrow-derived mesenchymal stem cells (BMSCs) to the injury region with the bone marrow by drilling subchondral bone in articular cartilage defects. This method is relatively simple and economic. However, there are disadvantages that the result is erratic and insufficient mesenchymal stem cells lead to impaired tissue regenerations [3-7].

Since mesenchymal stem cells can differentiate into bones, cartilages and fat cells and proliferate rapidly, they are an important source for repairing articular cartilages. In addition, the recent interest has focused on mesenchymal stem cells (MSC) to overcome the problems. In order to regenerate the damaged articular cartilages by MSCs, a sufficient number of MSCs are introduced into the cartilage defect and the gathered MSCs are attached to the articular cartilage matrix to proliferate and differentiate to chondrocytes such that the cartilage matrix has to be generated. In the spontaneous cure process, MSCs may migrate directly to the injury site and differentiate to articular chondrocytes. The condensation of MSCs and the interactions between cell-cell and cell-matrix is necessary for the chondrogenic differentiation of MSCs [8].

In the chondrogenic differentiation of MSCs, microenvironments surrounding cells play an important role.

Interactions between MSCs and collagens adjacent MSCs promote the chondrogenic differentiation of MSCs.

A sufficient number of BMSCs seeding into the cartilage defect are very important for treating various damaged tissues including cartilage [11-13]. A phenomenon, in which MSCs circulating in blood or bone marrow gather into the cartilage defect, is called homing. The homing in MSCs is achieved over several stages by cell adhesion proteins and chemokines [14-17]. Chemokine is a small cytokine of approximately 810 kDa. Approximately 50 types of chemokines have been known, and they are in charge of inducing chemotaxis of various cells [18-20]. Chemokines bind to chemokine receptor, which is kind of a G-protein receptor, to induce chemotaxis. Currently, Approximately 19 types of chemokine receptors have been reported. In addition, skin tissue regeneration using chemokines have been reported in MSCs [21-23].

Conventional treatments used for articular damages (for example, drug therapy, surgery, gene therapy, etc.) rarely give the desired result. Besides, considering physical characteristics of implants, autologous or allogeneic bone-cartilage tissue is transplanted, or the autologous chondrocytes transplantation is performed to supply a sufficient number of chondrocytes. They exhibit better therapeutic effects than the other treatments. However, there are many difficulties in the actual transplantation due to limitations of donation parts or donors, high-cost, repeat surgeries and significantly impaired functions of the transplanted cells.

Although artificial substitutes composed of complexes in which biodegradable synthetic polymer are coated with cells has been recently attempted to clinical applications, they have not been able to overcome the current problems. Likewise, various methods for regenerating the damaged articular cartilage tissues have been developed, but it is limited and insufficient to clinical applications.

Therefore, there remains an urgent need in the art to develop cell-based therapeutic approaches to overcome the existing shortcomings with maintaining characteristics of cells.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THIS INVENTION

Technical Purposes of this Invention

The present inventors have made intensive studies to develop an effective method for inducting migration of a cell, which is necessary for treating a damaged tissue, into the damaged tissue. As results, they have found that IL (interleukin)-8 and MIP (Macrophage Inflammatory Protein)-3α as chemokines enhance recruitment of mesenchymal stem cells (preferably, bone marrow-derived mesenchymal stem cells) or keratinocytes with high efficiency. Therefore, the damaged tissue may be treated by implanting biodegradable scaffolds including the chemokines in more simple and effective manner.

Accordingly, it is an object of this invention to provide an implantable composition for treating a damaged tissue.

It is another object of this invention to provide a method for inducting in vivo migration of a therapeutic cell into a damaged tissue.

Other objects and advantages of the present invention will become apparent from the following detailed description together with the appended claims and drawings.

Technical Solutions of this Invention

In one aspect of this invention, there is provided implantable composition for treating a damaged tissue, comprising a biodegradable scaffold as an active ingredient, wherein the biodegradable scaffold comprises at least one chemotactic factor selected from the group consisting of IL (interleukin)-8, MIP (Macrophage Inflammatory Protein)-3α, and derivatives thereof.

The present inventors have made intensive studies to develop an effective method for inducting migration of a cell, which is necessary for treating a damaged tissue, into the damaged tissue. As results, they have found that IL (interleukin)-8 and MIP (Macrophage Inflammatory Protein)-3α as chemokines enhance recruitment of mesenchymal stem cells (preferably, bone marrow-derived mesenchymal stem cells) or keratinocytes with high efficiency. Therefore, the damaged tissue may be treated by implanting biodegradable scaffolds including the chemokines in more simple and effective manner.

The present inventors have selected chemokine receptors which are expressed in human BMSCs and over-expressed under in vitro injury, and they have induced the homing of MSCs by implanting biodegradable scaffolds including the ligands of the chemokine receptors to a damaged bone tissue, an articular tissue or a skin tissue. Therefore, they have found that the damaged bone tissue, articular tissue or skin tissue may be treated effectively.

The term used herein "chemotaxis" refers to the movements of motile cells with positive direction (i.e., the direction toward stimulus) or negative direction (i.e., a direction away from the stimulation) in response to a chemical stimulus. The cell membranes are activated by the corresponding chemotactic factor (chemotactic substances; chemokine), which is mediated by the corresponding cell surface receptor (chemokine receptor).

The term used herein "chemotactic factor" refers to extracellular matrix molecules and the secreted proteins activating chemotaxis by spreading from the tissues, for example, TGF (transforming growth factor) family, BMP (bone morphogenetic protein) family, CDMP (cartilage-derived morphogenetic proteins), FGF (fibroblast growth factor) family, CTGF (connective tissue growth factors), PDGF (platelet-derived growth factor) family, VEGF (vascular endothelial growth factor) family, extracellular matrix molecules (e.g, osteopontin, fibronectin, hyaluronic acid, heparin, thrombospondin, collagen, vitronectin, etc.) and chemokines.

According to a preferred embodiment, the present chemotactic factor includes chemokines.

Chemokine is a protein (5-20 kDa) that plays an important role for physiological functions in various processes such as hematogenous functions of hematopoietic stem cells and chemotaxis of leukocytes.

Amino acid sequences of all chemokines are similar and may be characterized by consecutive sequences of 4 cysteines. The chemokine family is divided into four sub-families: (a) CCL; (b) CXCL; (c) CX3CL; and (d) XCL (Murphy, et al., International union of pharmacology, XXII, Nomenclature of chemokine receptors, Pharmacol Rev, 52: 145-176 (2000)).

According to a preferred embodiment, the chemokine which may be used in present invention includes CCL20 (MIP-3α), CCL19, CCL21, CCL27, CCL28, CXCL8 (IL-8), CXCL9, CXCL10, CXCL11, CXCL12 (SDF-1), CXCL16, CXCL13, CXCL5, CXCL6, CCL2 (MCP-1), CCL8, CCL13, CCL25, CCL3, CCL4, CCL5, CCL7, CCL14, CCL15, CCL16, CCL23, CX3CL1, XCL1, XCL2, CCL1, CCL17, CCL22, CCL11, CCL24, CCL26, CXCL1, CXCL2, CXCL3 and CXCL7, more preferably CCL20, CCL19, CCL21, CCL27, CCL28, CXCL8, CXCL9, CXCL10, CXCL11, CXCL12, CXCL16, CXCL13, CXCL5, CXCL6, CCL2, CCL8, CCL13 and CCL25, still more preferably CCL20, CXCL8, CCL2, and CXCL12, and most preferably CCL20, and CXCL8.

The amino acid sequences of CCL20 and CXCL8 are respectively described in SEQ ID NOs:1 and 2.

According to a preferred embodiment, the chemokine concentration which may be used in present invention is 10-1,000 ng/ml per biodegradable scaffold (1 g), more preferably 20-800 ng/ml per biodegradable scaffold (1 g), still more preferably 35-700 ng/ml per biodegradable scaffold (1 g), and most preferably 50-500 ng/ml per biodegradable scaffold (1 g).

The term used herein "biodegradable scaffold" refers to a three-dimensional structure consisting of biodegradable polymer containing the chemotactic factor. It functions as a scaffold inducing cell migration, which is necessary for regeneration of the damaged tissue, into target locations (e.g, the damaged articular tissue or skin tissue.) by implanting. Preferably, the present biodegradable scaffold is the biocompatible material. It usually forms porous micro-scaffolds to provide physical supports for the migrating cells. It is provided to recruit cells for treatment or regeneration.

The present biodegradable scaffold has the chemotaxis, whereby the homing of the cells (preferably, stem cells or keratinocytes) required for the damaged tissue is promoted. The recruited cells exhibit regeneration effects in the damaged target area.

Figure 2A:
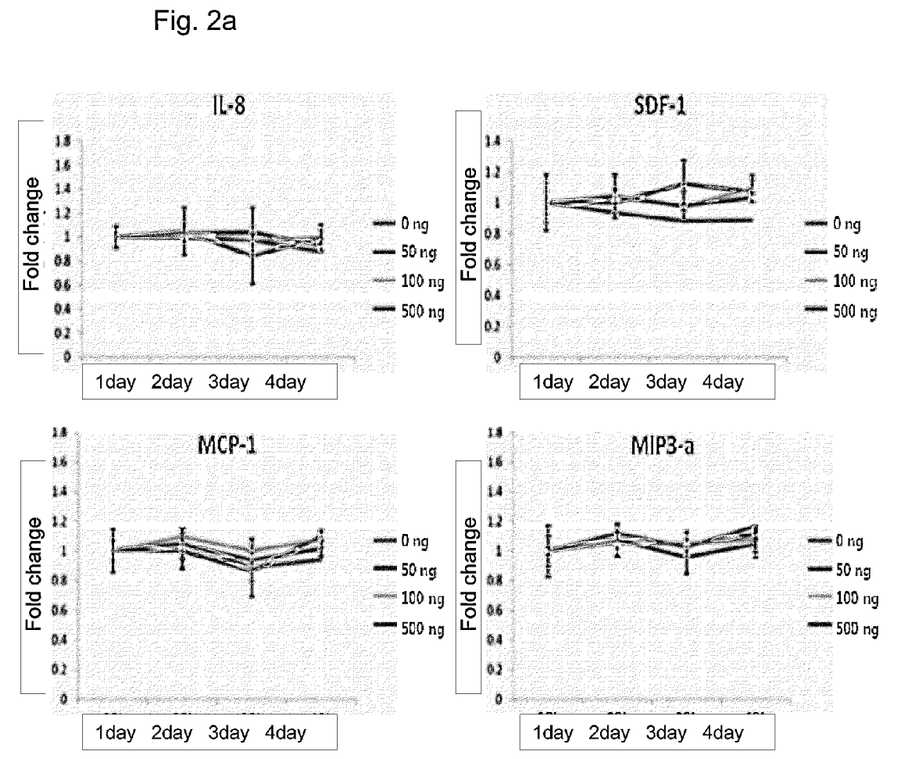
FIG. 2a shows results of the cell proliferation.
Figure 2B:
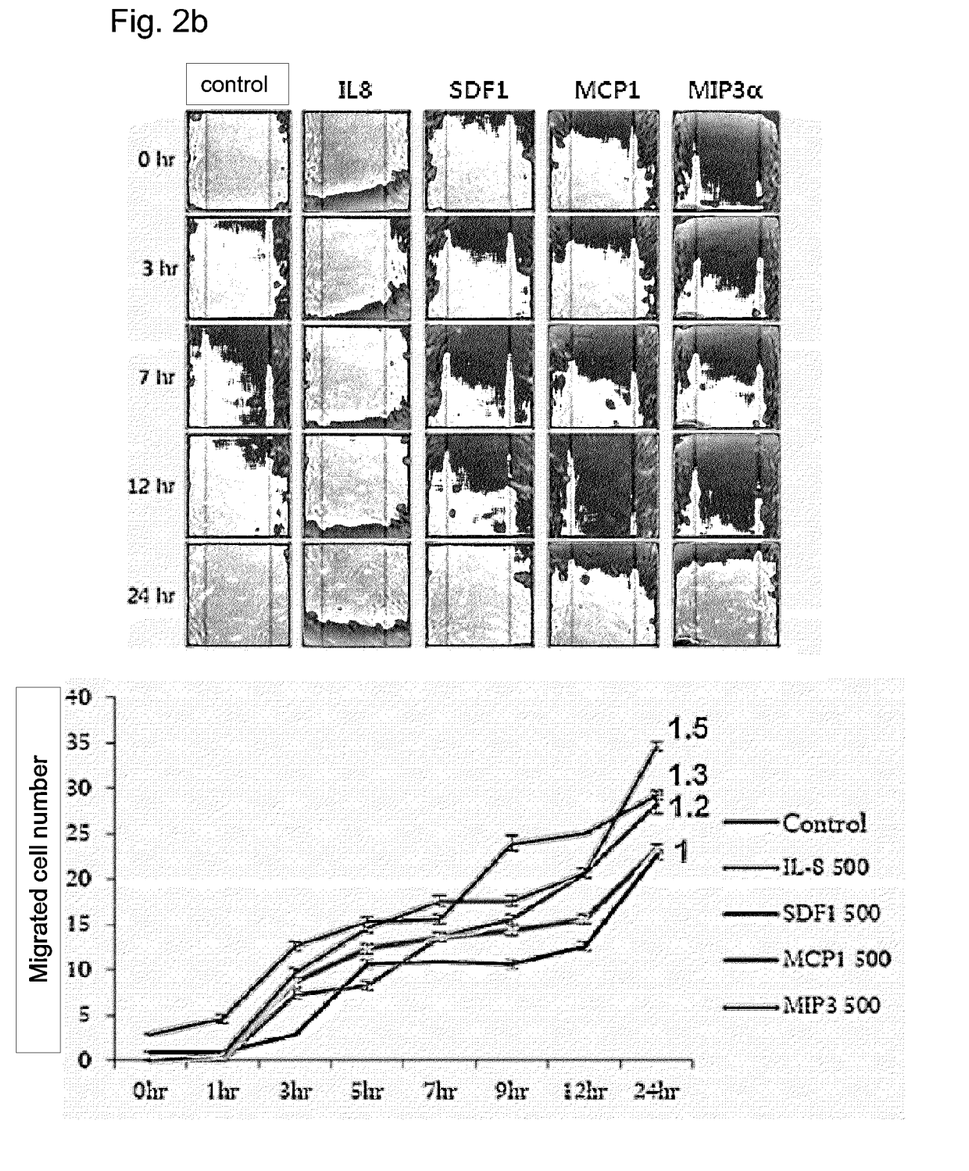
FIG. 2b shows results of the wound healing.
Figure 2C:
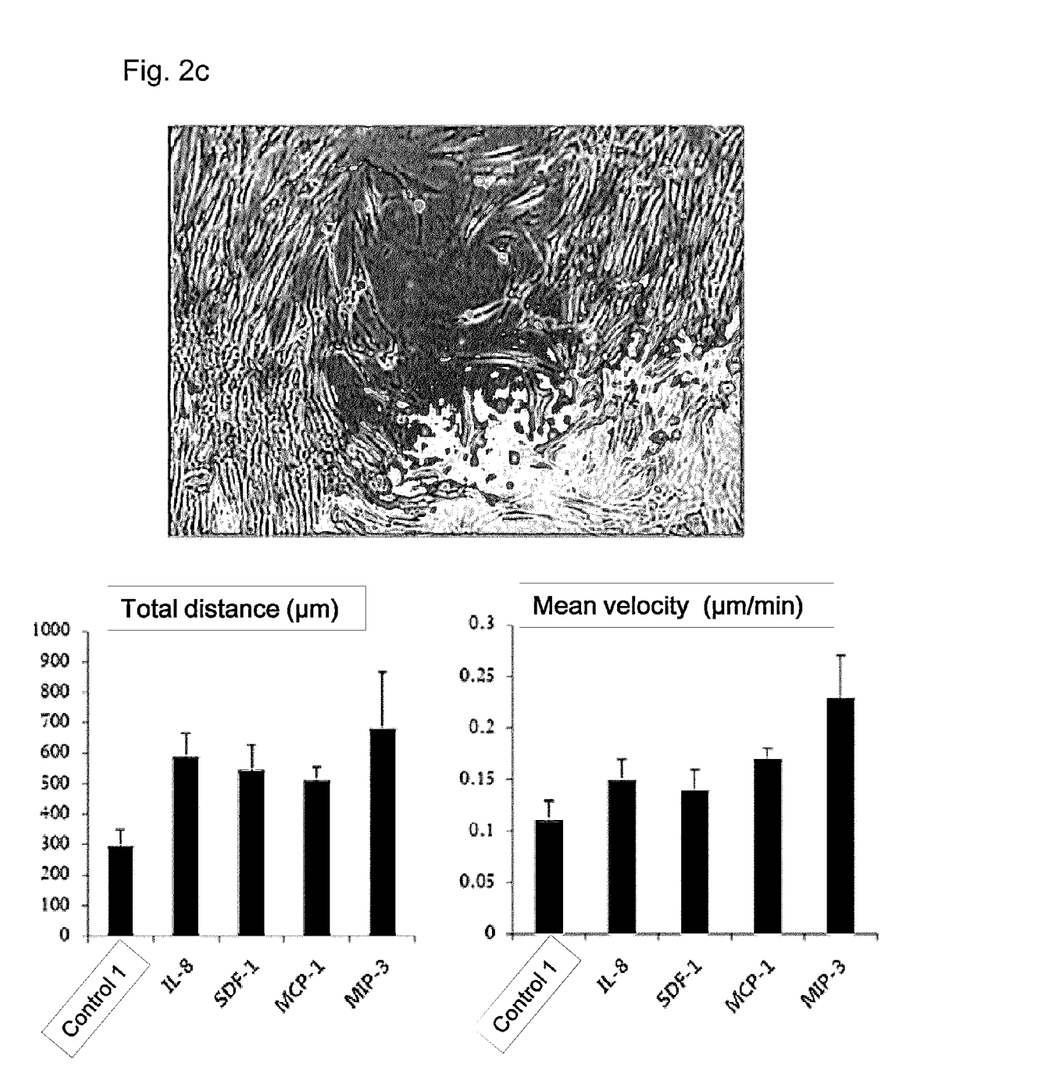
FIG. 2c shows results of the migratory capacity.
Figure 3A:
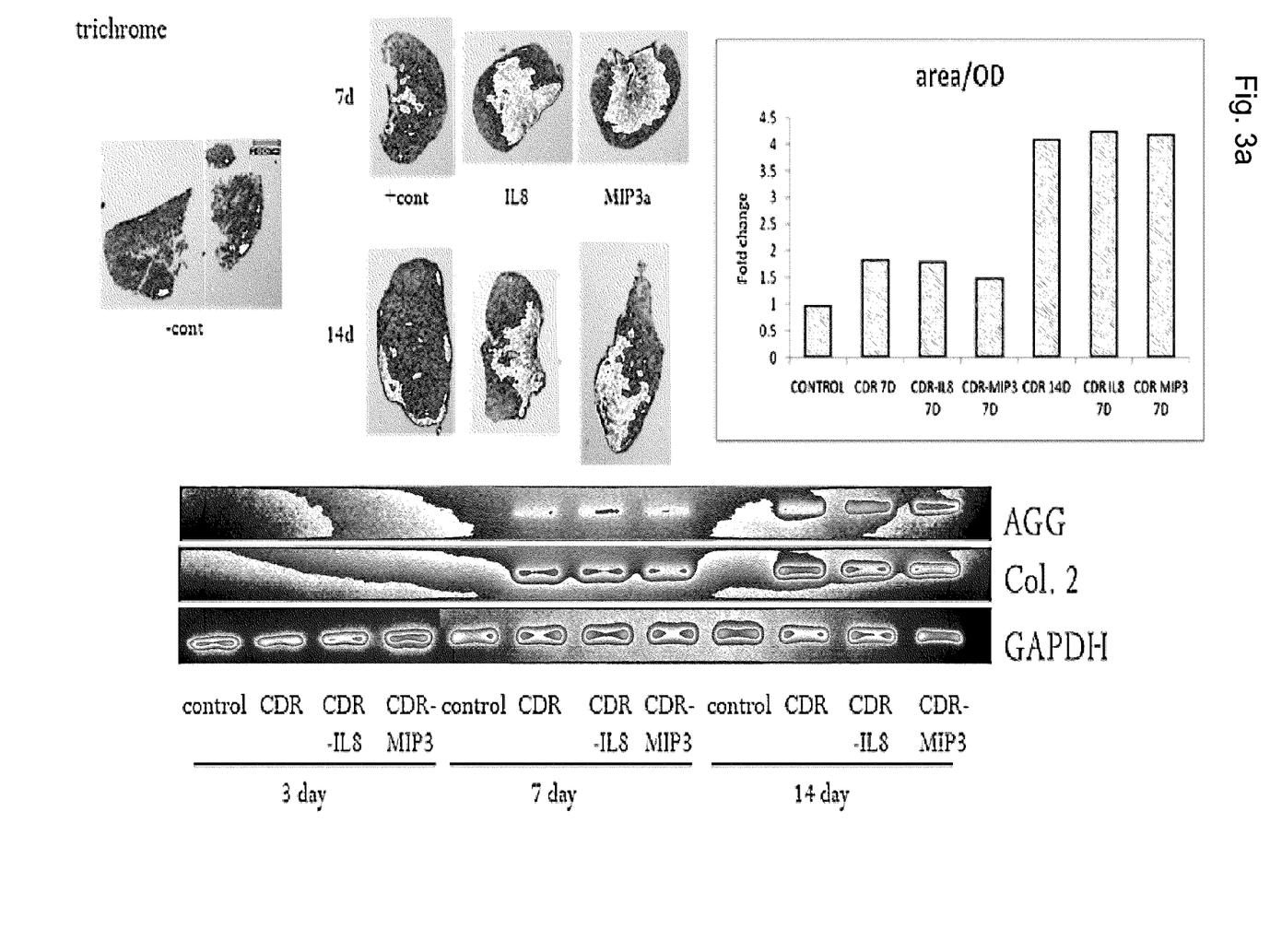
Figure 3B:
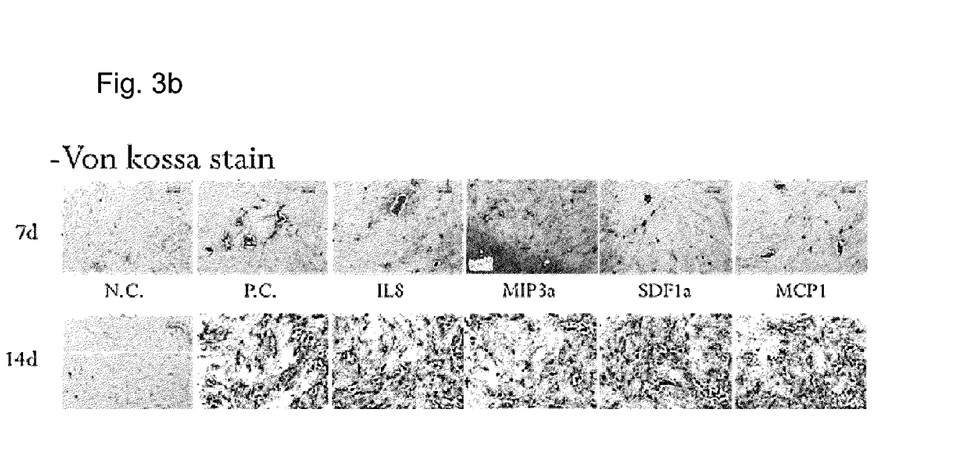
FIG. 3b shows results of Von kossa staining. Abbreviations: N.C., negative control group; and P.C., positive control group.

According to the present invention, the implantation of the present biodegradable scaffold significantly increased the number of the migrated cells (FIGS. 2b and 4d), cell migration distance and velocity (FIG. 2c). In addition, the implantation increased only cell migration, and there was no influence to cell differentiation (FIG. 3). It means that the present biodegradable scaffold only promotes recruitments of the cells necessary for the damaged tissue regeneration.

According to a preferred embodiment, the present biodegradable scaffold may be used with any size, shape or composition under degradable conditions.

According to a preferred embodiment, the present biodegradable scaffold is selected from the group consisting of a PLGA (poly(lactic-co-glycolic acid)), a PLA (polylactic acid), a PGA (polyglycolic acid), a PCL (poly-ε-caprolactone), a PAA (poly(amino add)), a poly(anhydride), a polyorthoester, a collagen gel, a hydro gel, hydrogel, a polyvinyl alcohol sponge, a gelatin, a polysaccharide, a polyphosphazene, a polyacrylate, a polyethylene oxide-propylene glycol block copolymer and mixture thereof, more preferably a PLGA (poly(lactic-co-glycolic acid)), a PLA (polylactic acid), a PGA (polyglycolic acid), a PCL (poly-ε-caprolactone), a PAA (poly(amino acid)), a polyorthoesther and derivative thereof, copolymer and mixture thereof, and most preferably a PLGA.

According to a preferred embodiment, the damaged tissue which is treated by the present composition is a bone tissue, an articular tissue or a skin tissue.

Once articular cartilages are destroyed, chondrocytes do not nearly migrate to the injury region and the injured articular cartilages do not recover spontaneously. Although the methods for treating the injured articular cartilage are subchondral drilling and autologous chondrocyte transplantation, they have disadvantages as follows: (a) repeated surgery; (b) limitations of the donor part; and (c) difficulties of a sufficient influx of MSCs.

The recent interest has focused on MSCs as source for repairing articular cartilages to overcome the problems.

MSCs are nonhematopoietic stromal cells which may differentiate and regenerated into mesenchymal tissues such as bones, cartilages, muscles, ligaments, tendons and fat, and they may be presented in various tissues. For instance, MSCs have been known to exist in bone marrow with the small number (for example, approximately 1 cell per 10,000 mononuclear cells). In addition, although MSCs may be immortalized, MSCs may have abilities to proliferate with maintaining pluripotency. In addition, MSCs trafficking and tissue homing are not exactly understood even though MSCs are appeared to migrate into the damaged tissue. For example, the chemokine and its receptor CXCR4 has been known to important in hematopoietic stem cells and cancer metastasis (Zou Y R, et al., Function of the chemokine receptor CXCR4 in haematopoiesis and in cerebellar development, Nature, 393:595-599 (1998)). However, necessity of CXCR4 expression in MSC in vitro migration and MSC in vivo homing has been evaluated. In addition, several studies have been reported that the MSCs transplanted into damaged tissues may induce recovery. However, it was determined that only limited MSCs were differentiated into the regenerated tissue. This discrepancy may be explained for the following reasons: (a) technical difficulties of separating MSCs in the regenerated tissue; (b) identification of MSC differentiation level in therapeutic step; and (c) possibilities for regeneration induction of MSC by MSC activation mechanism rather than MSC differentiation.

As mentioned above, although numerous studies have been clinically applied MSCs, developments of effective methods for exhibiting in vivo therapeutic effects by recruiting of MSC into the damaged tissue are still insufficient.

The present composition contributes to tissue regeneration by homing MSCs into damaged bone tissues other than articular tissues, whereby bone-related diseases may be treated. A bone tissue in which the present composition may be implanted includes all skeleton bones of the body including ribs, skull, long bones, humerus, vertebrae, pelvic bones and blade bone, but is not limited thereto.

According to a preferred embodiment, an articular tissue in which the present composition may be implanted includes hip joint, shoulder, knee, ankle, wrist, elbow, tarsal bone, ulna, vertebra, wristbone, metacarpus and temprormandibular joint, but is not limited thereto.

The present damaged articular tissue includes hyaline cartilage (for example, hyaline cartilage in joints, nose, larynx or sternum), elastic cartilage (for example, elastic cartilage in ear) and fibrocartilage (for example, a disc), but is not limited thereto.

A bone or articular disease which may be treated by the present composition includes arthritis such as osteoarthritis and rheumatoid arthritis, osteoporosis, osteochondrosis, osteochondritis, osteogenesis imperfecta, osteomyelitis, osteophytes, achondroplasia, costochondritis, chondroma, chondrosarcoma, herniated disk, Klippel-Feil syndrome, osteitis deformans; osteitis fibrosa cystica, accidental tissue defect, fracture, wound, joint trauma, tissue defect-related articular cartilage diseases by autoimmune disorders, diabetes and cancer, but is not limited thereto.

The present composition also may be used for regenerating and treating damaged skin tissues. According to the present invention, the selected chemotactic factors IL-8 and MIP-3α in the present invention significantly increases the recruitment of human keratinocytes into the damaged skin tissues, whereby regenerations of epidermis, hypodermis and subcutaneous tissue may be promoted.

The term used herein "keratinocyte" encompasses "skin cell", "corneous cell", "basal cell" or "basal keratinocyte" in the art.

The regeneration or wound healing of skin is achieved through various processes such as immune response, reepithelialization, granulation, fibroplasia, contraction, and migration, proliferation and differentiation of keratinocytes play an important role in a series of processes of skin regeneration. Keratinocytes accounts for 95% of epidermis which composes the outermost layer of the skin. Its primary function is forming protective barrier from external damage such as pathogens (bacteria, parasites, viruses, etc.), heat, ultraviolet light and loss of moisture. Keratinocytes are generated in the basal layer and raised toward granular layer. The keratinocytes produce keratin. The generated keratin replaces the existing cell compositions and skin tissues and ultimately helps the regeneration of skin. Therefore, the present composition may be applied to a composition for treating skin diseases since the present composition induces migration of keratinocytes into the damaged tissue efficiently.

A skin disease which may be treated by the present composition includes burns, frostbite, wound, keloids, chemical destruction of tissue, abrasion, bone necrosis, laceration, avulsion, penetrated wound, cuts, contusion or bruise, skin ulcers, skin keratosis, decubitus ulcer and acne, but is not limited thereto.

According to a preferred embodiment, a skin tissue in which the present composition may be implanted includes epidermis, hypodermis and subcutaneous tissue, but is not limited thereto.

According to a preferred embodiment, cells which are induced to recruit in the present invention is stem cells or keratinocytes. The stem cells include autologous stem cells or non-autologous stem cells, preferably autologous stem cells, more preferably mesenchymal stem cells (MSCs) or ectodermal stem cells, and the most preferably bone marrow-derived mesenchymal stem cells or keratinocyte stem cell.

The present composition mat be provided as pharmaceutical composition including (a) a therapeutically effective amount of the biodegradable scaffold described as above; and (b) a pharmaceutically acceptable carrier.

The term used herein "therapeutically effective amount" means an amount sufficient to achieve the treatment effect or activity to the damaged tissue.

When the composition of the present disclosure is prepared as a pharmaceutical composition, the pharmaceutical composition of the present disclosure may comprise a pharmaceutically acceptable carrier. The pharmaceutical composition may contain a pharmaceutically acceptable carrier. In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

The pharmaceutical composition according to the present invention may be administered directly into the damaged tissue, i.e., by subcutaneous, intramuscular, transdermal, intraarticular injection.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition.

According to the conventional techniques known to those skilled in the art, the pharmaceutical composition may be formulated with pharmaceutically acceptable carrier and/or vehicle as described above, finally providing several forms including a unit dose form and a multi-dose form. The formulation may be in the form of a solution in oily or aqueous medium, a suspension, a syrup, a emulsion, an extract, an elixir, a powder, a granule, a tablet or a capsule, and may further include a dispersant or stabilizer.

According to a preferred embodiment, the present composition may be applied to a mammal, and more preferably a damaged joints (e.g, articular cartilage), or a skin tissue.

According to a preferred embodiment, the mammal is not particularly limited, preferably it includes human, mouse, rat, rabbit, monkey, pig, horse, cow, sheep, antelope, dogs and cats, and more preferably human and mouse.

In another aspect of this invention, there is provided a method for inducting in vivo migration of a therapeutic cell to a damaged tissue, comprising:

(a) soaking a biodegradable scaffold into a solution comprising at least one chemotactic factor selected from the group consisting of IL (interleukin)-8, MIP (Macrophage Inflammatory Protein)-3α, and derivatives thereof; and (b) implanting the biodegradable scaffold to a damaged tissue.

In still another aspect of this invention, there is provided a method for treating a damaged tissue, comprising:

(a) soaking a biodegradable scaffold into a solution comprising at least one chemotactic factor selected from the group consisting of IL (interleukin)-8, MIP (Macrophage Inflammatory Protein)-3α, and derivatives thereof; and (b) implanting the biodegradable scaffold to a damaged tissue.

Since the chemotactic factors and the biodegradable scaffold used in the present method are already described as above, the common descriptions between them are omitted in order to avoid undue redundancy leading to the complexity of this Specification.

Effects of this Invention

The features and advantages of the present invention will be summarized as follows:

(a) The present invention provides an implantable composition for treating a damaged tissue and a method for inducing an in vivo migration of a cell for treatment to a damaged tissue region.

(b) The present invention may treat the damaged tissue by inducing/promoting homing of a cell for tissue generation by implanting a biodegradable scaffold reacted with chemotactic factors (for example, IL-8 or MIP-3α) to a damaged location (for example, joint cartilage or skin).

(c) Therefore, the composition of the present invention can not only be applied to the treatment of a damaged bone tissue, a joint cartilage, or a skin tissue more conveniently and efficiently compared to the conventional technology, but can also be used as a useful treatment supplement agent in cell treatment using allogeneic cell by enabling efficient utilization of cell resources for treatment, the cell resources which are high in scarcity.

BRIEF DESCRIPTION OF THE DRAWINGS

FIGS. 2a-c represent effects of chemokines in cell proliferation and migration.

FIGS. 3a-b represent effects of chemokines in cell differentiation. The top panel of FIG. 3a shows results of Masson trichrome staining, and the bottom panel of FIG. 3a shows results of gene expressions in cartilage markers.

BEST MODE FOR CARRYING OUT THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Cell Culture

Human bone marrow-derived mesenchymal stem cells (BMSCs) were aspirated from the posterior iliac crest of patients after approval by the Institutional Review Board (IRB), centrifuged to precipitate pellet. The resultant supernatant was isolated, wished and seeded with DMEM-LG (Dulbecco's modified eagle's medium-low glucose; GIBCO-BRL, Grand Island, N.Y., USA) containing 10% FBS (fetal bovine serum; GIBCO BRL, Grand Island, N.Y., USA), 100 units/ml of penicillin G (GIBCO) and 0.1 mg/ml of streptomycin (GIBCO) into T-75 cm² cell flask (Falcon, Germany), followed by incubating for 4 days. Then, cells unattached to the bottom of the flask were removed. The MSCs attached to the bottom of the flask were exchanged with media every 3 days, and sub-cultured until nearly 90% confluent. BMSCs (passage 2-3) were used in all experiments.

In Vitro Mimicking of Articular Cartilage Injury

After serum starvation of BMSCs in serum-free DMEM-LG for 12 hours, cells were stimulated by adding 10 ng/mL of interleukin-1beta (IL-1β, R&D Systems Inc., Minneapolis, Minn., USA) or 10 ng/mL of tumor necrosis factor-alpha (TNF-α, R&D Systems Inc.) to the media for 4, 24, or 48 hours. The stimulated cells were used for our experiments.

Reverse Transcriptase-Polymerase Chain Reaction

Total RNA was isolated from BMSCs using an RNeasy kit (Qiagen, Valencia, Calif., USA). RT-PCR was performed to evaluate expression of 19 chemokine receptors including CCR1-10, CXCR1-7, CX3CR and XCR1 (Table 1). The amplified DNAs of chemokine receptor were subject to DNA sequence analysis using Genetic Analyser (Applied BiosystemsInc., Foster City, Calif., USA). As a result, it was verified that there were no overlapping sequences each other.

TABLE 1

Primer sequences used for RT-PCR

| Gene | Size (BPs) | | Sequence (5'-> 3') |
|---|---|---|---|
| CCR1 | 560 | Forward | AGGTTCTGACTCTTGGCACA |
| | | Reverse | TCTCGTTAGGTCTCAACTCT |
| CCR2 | 580 | Forward | CCAAACTACCTTCCAGTTCC |
| | | Reverse | AGCTTCTCCACCTTCCATTC |
| CCR3 | 699 | Forward | CCTAGTGAGAAGCTGGAAAG |
| | | Reverse | CCTCTGCAATGTCAGATTGG |
| CCR4 | 501 | Forward | CTTGCACCAAAGAAGGCATC |
| | | Reverse | GGAGTTGAGAGAGTACTTGG |
| CCR5 | 550 | Forward | TTCTATGAGGCAACCACAGG |
| | | Reverse | TTCCCTCACCTTACCTGTAC |
| CCR6 | 540 | Forward | CTCCGATCCAGAACACTACC |
| | | Reverse | CCACAGGTCCTTCAAGATCT |
| CCR7 | 548 | Forward | CAAGAGGCTCAAGACCATGA |
| | | Reverse | ACCACAGCGATGATCACCTT |
| CCR8 | 560 | Forward | AGTTCAGCATGAAGGATGCC |
| | | Reverse | TGAGGCATTGTGTTTGATGG |
| CCR9 | 580 | Forward | TGACATCTGCTTCCAGGTCA |
| | | Reverse | CTGAAGCCACAGAAGTTCAC |
| CCR10 | 489 | Forward | TCTTCCTGGCCTGTATCAGC |
| | | Reverse | AGTGCGACATCCTTGCGTTT |
| CXCR1 | 520 | Forward | GACCAACATCGCAGACACAT |
| | | Reverse | GTGAGCTCACATAGCTTGAG |
| CXCR2 | 520 | Forward | GTTCCTCCCTTCTCTTCACA |
| | | Reverse | CTGAGACAGAGTCTCACTGT |
| CXCR3 | 528 | Forward | CCAGACTTCATCTTCCTGTC |
| | | Reverse | AGGTCTCAGACCAGGATGAA |
| CXCR4 | 517 | Forward | ACACAGTCAACCTCTACAGC |
| | | Reverse | CTCGGTGATGGAAATCCACT |
| CXCR5 | 490 | Forward | GAAACGCATGCCTGGTTCAC |
| | | Reverse | ACCTAGAACGTGGTGAGAGA |
| CXCR6 | 518 | Forward | TTCTTCTTGCCACTGCTCAC |
| | | Reverse | AAACAAAGCCTGCCTCACCA |
| CXCR7 | 516 | Forward | AACTTCTCGGACATCAGCTG |
| | | Reverse | GGTCTTCAGGTAGTAGGTGT |

TABLE 1-continued

Primer sequences used for RT-PCR

| Gene | Size (BPs) | | Sequence (5'-> 3') |
|---|---|---|---|
| CX3CR | 539 | Forward | GATCTGCTGTTTGTAGCCAC |
| | | Reverse | CATAGAGCTTAAGCGTCTCC |
| XCR | 550 | Forward | GAGTCCCTCACCAACATCTT |
| | | Reverse | ACAGGGTGAAGTTGTAGGGA |
| GAPDH | 444 | Forward | ATCACTGCCACCCAGAAGAC |
| | | Reverse | ATGAGTCCACCACCCTGTT |

Reverse Dot-Blot Hybridization

To select chemokine receptor over-expressed by IL-1β or TNF-α, sample DNA of 19 chemokine receptors were amplified using RT-PCR. cDNA of IL-1β or TNF-α-stimulated human BMSCs for 4, 24, or 48 hours were synthesized using Omniscript RT Kit (Qiagen) to use probe cDNA. Sample DNAs were dotted onto nylon membranes (Amersham, GE healthcare, UK) and irradiated with ultraviolet (1200×100 μjoules) to fix. The probe cDNAs were labeled using Rediprime II random prime labeling system (GE Healthcare UK Limited. Amersham Place, Little Chalfont, Buckinghamshire, UK) and $\gamma^{32}$P-dCTP (NEN Life Sciences, Boston, USA). The membranes were hybridized with the probe cDNAs at 42° C. for 15 hours. After washing of membranes, radioisotope-labeled sample signal was detected by fluorescent image analyzer (FLA-7000, Fujifilm, Japan). The obtained images of hybridized sample were quantitated with a densitometry (TINA pixel analyzer version 2.10, Raytest Isotopen megerate GmbH, Straubenhardt, Germany). Statistical significances of the quantitated values were validated using paired t-tests (P-value<0.05).

Effects on Cell Proliferation

To determine effects on cell proliferation, MSCs were treated with 50-500 ng/ml of chemokine and incubated for 1, 2, 3 and 4 days. After chemokine stimulation, cell proliferations were measured by MTT assay, respectively.

Effects on Cell Differentiation

For inducing differentiation to chaondroblasts, MSCs incubated in DMEM-LG [10% FBS (GIBCO), 1% antibiotics (antibioticantimycotic) solution (GIBCO)] containing 10 ng/ml of TGF-β3 (R & D system Inc, Minneapolis, Minn., USA) and 30 μg/ml ascorbic acid (Sigma Co., St. Louis, Mo., USA) for 14 days to induce the chondrogenic differentiation. The differentiated levels of the TGF-β3-treated MSCs were analyzed by comparing with that of the TGF-β3-nontreated MSCs. For inducing differentiation to osteoblasts, MSCs incubated in DMEM-LG containing osteoblast differentiation solution [10 mM β-glycerophosphate (Sigma), 100 μM dexamethasone (Sigma) and 50 μg/ml ascorbic acid-2-phosphate (Sigma)] for 14 days to induce the osteogenic differentiation. The differentiated levels of the osteoblast differentiation media-treated MSCs were analyzed by comparing with that of the osteoblast differentiation solution-nontreated MSCs.

Wound Healing Assay and Cell Migratory Capacity

MSCs were cultured using silicon culture inserts (IBIDI, Germany). MSCs were treated with 500 ng/mL of chemokine. The wound healing levels were analyzed by counting the number of cells which migrated to the wounded area. In addition, the cell migration distance and velocity were measured by tracking the migrating cells in real time.

Chemotaxis Analysis

MSCs were incubated using transwell insert with 8 μm pores (Falcon, Germany), and the cells which migrated toward chemokines by passing through the micro-pore were counted to analyze in vitro chemotaxis. PLGA scaffolds (provided by Kim Soo hyun from Korea Institute of Science and Technology Biomaterials Center) containing IL-8 or MIP-3α were subcutaneously transplanted into nude mouse. After subcutaneous implantation of PLGA scaffolds, 1.5×10⁶ cells of the fluorescence-labeled MSCs were injected into blood vessel of the mouse tail vein. The movement of injected cells toward the chemokines (IL-8, MIP-3α) was tracked using Optix (ART, USA) to analyze in vivo chemotaxis.

Results

Chemokine Receptors Expressed in MSCs

Figure 1:
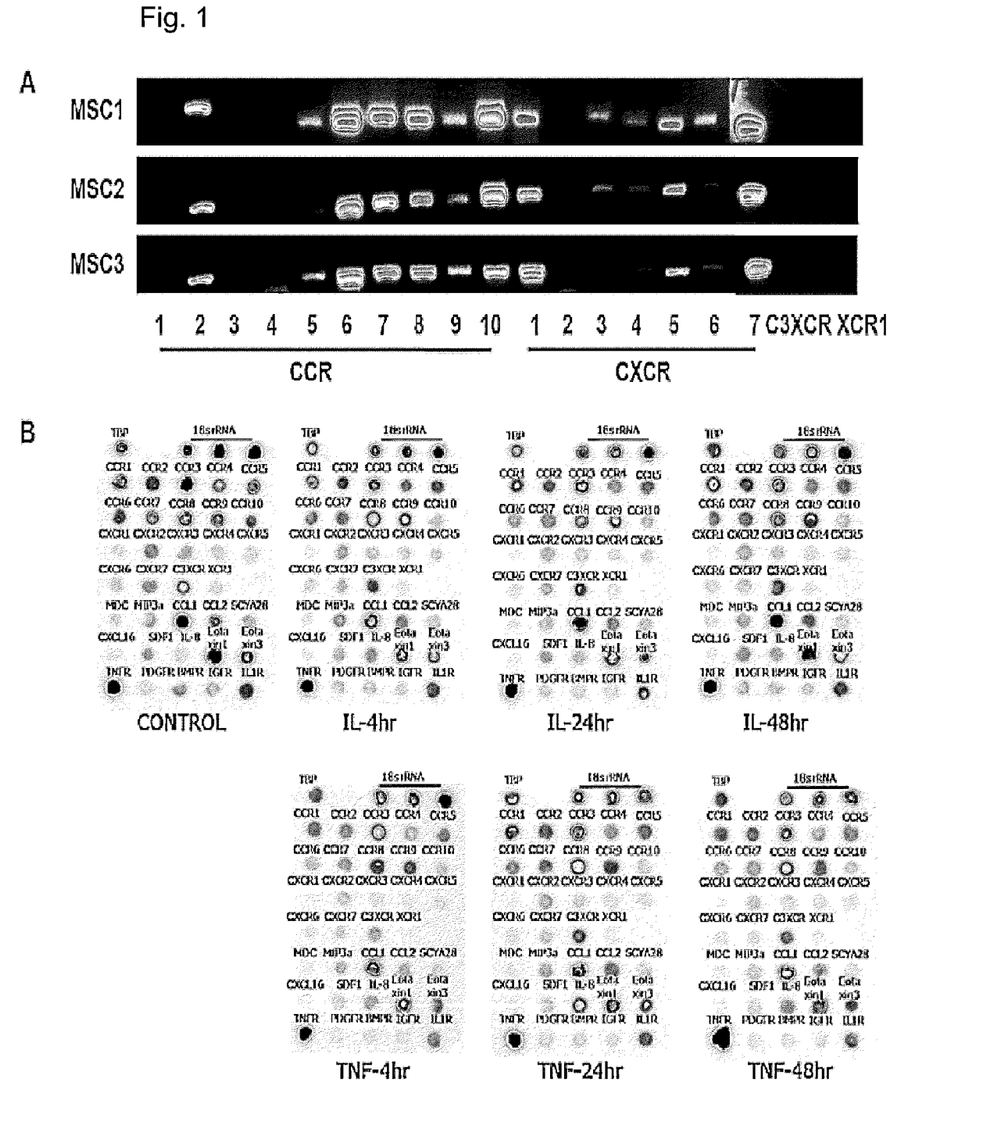
FIG. 1 represents gene expression changes of chemokine receptors by pro-inflammatory cytokines in human bone marrow-derived mesenchymal stem cells. A: RT-PCR; B: reverse dot-blot. Control group, normal mesenchymal stem cell group; IL-4 h, a group of probes from BMSCs stimulated by IL-1β for 4 hours; IL-24 h, a group of probes from BMSCs stimulated by IL-1β for 24 hours; IL-48 h, a group of probes from BMSCs stimulated by IL-1β for 48 hours; TNF-4 h, a group of probes from BMSCs stimulated by TNF-α for 4 hours; TNF-24 h, a group of probes from BMSCs stimulated by TNF-α for 24 hours; and TNF-48 h, a group of probes from BMSCs stimulated by TNF-α for 48 hours.

Primer sequences for Reverse transcription-polymerase chain reaction (PCR) are shown in Table 1. Sequences of genes amplified by primer sequences in Table 1 were subject to DNA sequence analysis. As a result, it was determined that the amplified gene sequences were not overlapped with those of the other chemokine receptors (data not shown). RT-PCR was performed to evaluate expression of 19 chemokine receptors in BMSCs (FIG. 1).

The amplified DNAs of chemokine receptor were subject to DNA sequence analysis using Genetic Analyser (Applied BiosystemsInc., Foster City, Calif., USA). As a result, it was verified that there were no overlapping sequences each other.

As a result of expression analysis of chemokine receptors in MSCs obtained from three or more donors, CCR2, CCR6, CCR7, CCR8, CCR9, CCR10, CXCR1, CXCR5, and CXCR7 were commonly expressed in MSCs from more than three donors.

Chemokine Receptors Increased the Expression in BMSCs on Articular Cartilage Injury As an articular cartilage is injured, IL-1β or TNF-α is released and these pro-inflammatory cytokines stimulate chondrocytes. The chondrocytes increase the releases of various chemotactic factors (23). Therefore, to examine the changes in the expression of chemokine receptors by pro-inflammatory cytokines, an in vitro cartilage injury condition was induced using treating IL-1β or TNF-α for 4, 24, or 48 hours, and Reverse Dot-Blot Hybridization was performed on human MSCs obtained from 3 donors. Although this study shows results of a representative donor, expression patterns of these chemokine receptors in MSC derived from three donors were determined to similar by repeating the experiment (FIG. 2). Results of Reverse Dot-Blot Hybridization were quantitated with a densitometry (TINA pixel analyzer version 2.10, Raytest Isotopen megerate GmbH, Straubenhardt, Germany). Based on the results, receptors increased by more than 2-fold change (fold change≥2) in expression levels were rearranged according to stimulation time. As a result, expressions of CCR2, CCR4, CCR6, CXCR1, CXCR2 and CXCR3 were commonly increased by more than 2-fold change in MSCs from three donors. Expression increase rates of the remaining chemokine receptors were not statistically significant.

In summary of the above results, chemokine receptors including CCR2, CCR4, CCR6 and CXCR1 were expressed significantly in normal MSCs, and the expressions of the chemokine receptors by pro-inflammatory cytokines were significantly increased in MSCs of three donors (more than 2-fold change).

Effects on Cell Migration

The migratory effects of chemokines selected as candidates were investigated using the wound healing assay. According to previous reports, SDF1 has been known to induce chemotaxis of MSCs through the CXCR4 and CXCR7 [17]. Therefore, in this study, the selected candidates were compared to SDF1. First, in order to elucidate wound healing effect caused by cell migration rather than cell proliferation, effects on cell proliferation were determined. As a result, cell proliferation was unaffected, and no cytotoxicity was observed by the chemokines at 50, 100 or 500 ng/ml of concentration (FIG. 2a). Among four kinds of candidates, IL-8 and MIP-3α exhibited the fastest wound healing effect at 500 ng/ml of concentration (FIG. 2b). Next, live-cell tracking of the wound healing assay was performed to measure the total distances and velocities of migrating MSCs. As a result, it was determined that the velocity and distance induced by MIP-3α were greater than those of the other chemokines (FIG. 2c).

Effects on Cell Differentiation

Effects by the candidates to osteogenic or chondrogenic differentiation induction of MSCs for 14 days were analyzed. As a result, it was determined that the candidates did not affect osteogenic or chondrogenic differentiation (FIG. 3). Therefore, the present chemokines are considered to promote the influx of autologous MSCs which are necessary for the regeneration of the damaged articular.

Chemotaxis Evaluation

Figure 4A:
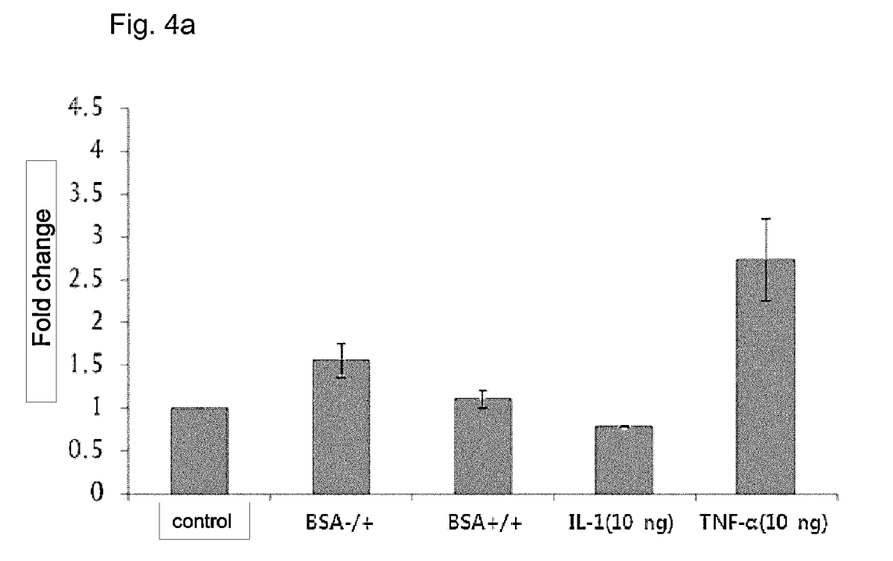
FIGS. 4a-d represent results of in vitro chemotaxis in bMSCs and keratinocytes, respectively.
Figure 4B:
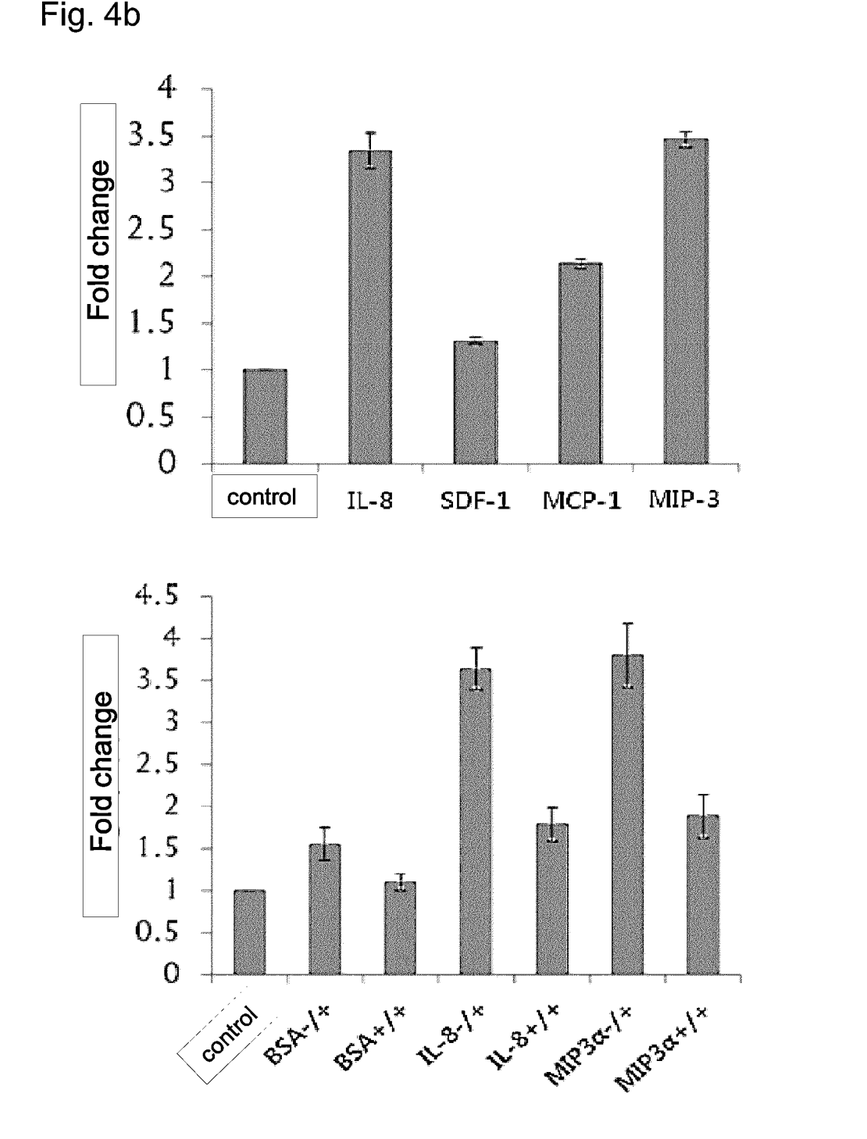
Figure 4C:
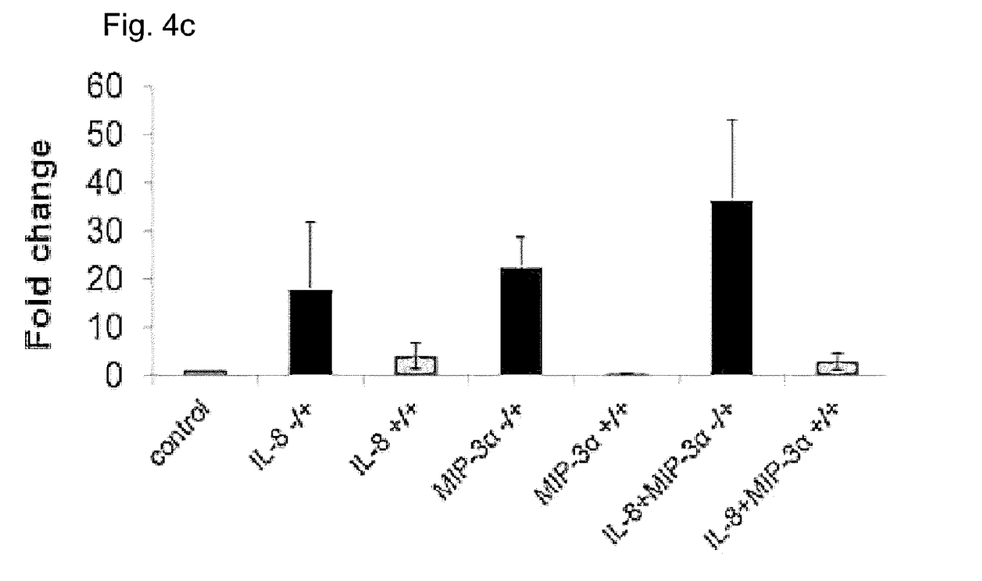
Figure 4D:
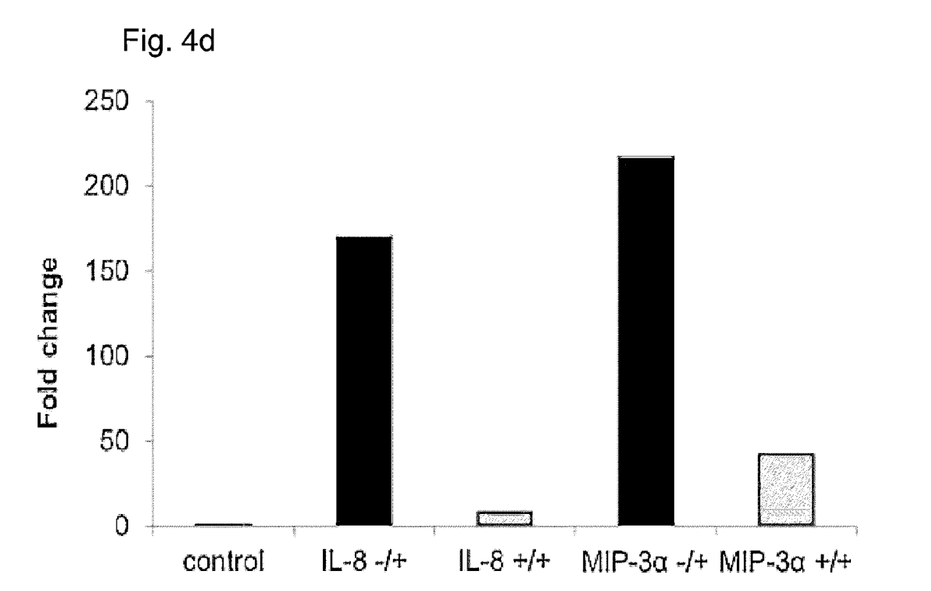
Figure 5:
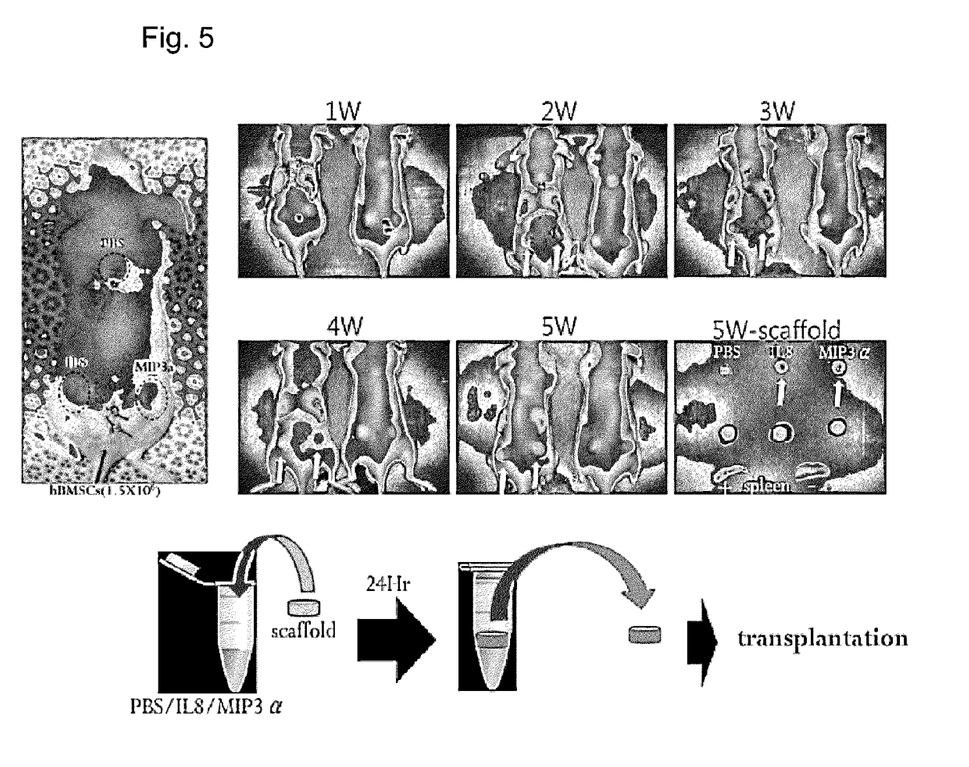
FIG. 5 represents results of in vivo chemotaxis in bMSCs. The top panel shows results of animal experiments (W, weeks), and the bottom panel schematically represents the diagram of the implantation of PLGA scaffold containing the chemokine.

Chemotaxis of the selected candidates for MSCs was evaluated in in vitro and in vivo. First, chemotaxis toward TNFα was observed in in vitro chemotaxis using transwell insert (FIG. 4a). Meanwhile, the chemotaxis of MSCs was significantly induced by MIP-3α and IL-8 (FIG. 4b) and it was significantly increased by using the combination of MIP-3α and IL-8 (FIG. 4c). In addition, the present inventors examined whether keratinocytes essential for skin tissue regeneration may be inflexed by IL-8 and MIP-3α in in vitro. As a result, IL-8 and MIP-3α induced the chemotaxis of keratinocytes (FIG. 4d). Based on these results, the present inventors elucidated the chemotactic effect of the two candidates (IL-8, MIP-3α) in in vivo. PLGA scaffolds containing PBS, IL-8 or MIP-3α were subcutaneously transplanted into nude mouse. After subcutaneous implantation of PLGA scaffolds, the fluorescence-labeled MSCs were injected into blood vessel of the mouse tail vein to track the migration of the injected MSCs. At 2 weeks later, it was determined that the injected MSCs migrated into the scaffolds containing IL-8 and MIP-3α. In addition, it was observed that cell migration was increased by 6 weeks post-injection (FIG. 5).

Visual Observation and Pathological Analysis

At 6 weeks post-operation, all the scaffolds were harvested from euthanized mice. H&E staining was performed to examine inflammation and the recruitment of inflammatory cells by chemokine-containing scaffolds.

Figure 6A:
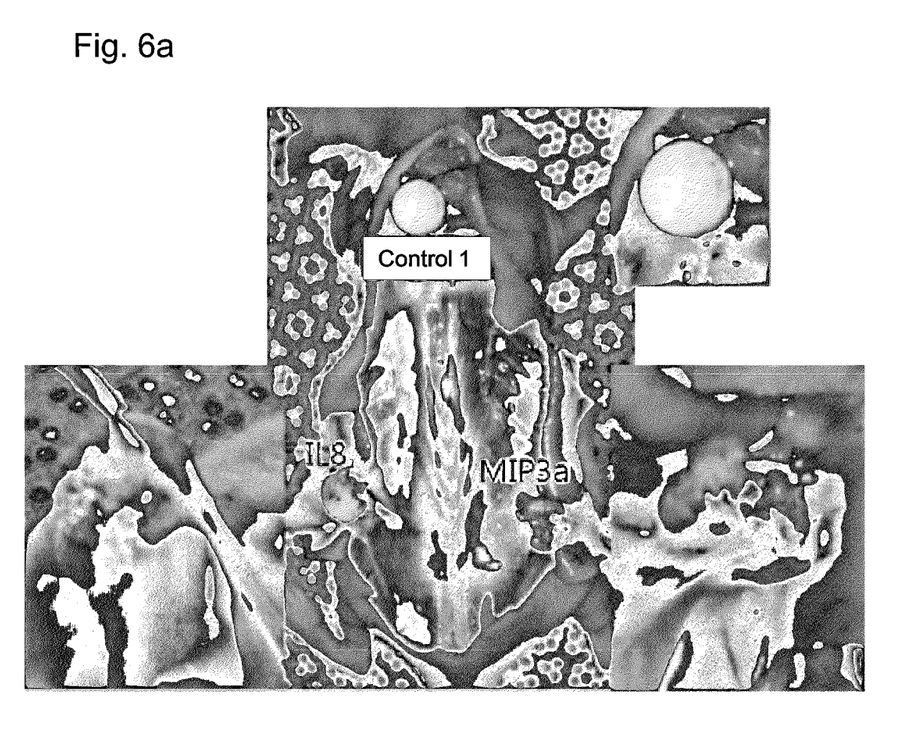
FIG. 6a represents images of visual observation after in vivo chemotaxis in bMSCs.
Figure 6B:
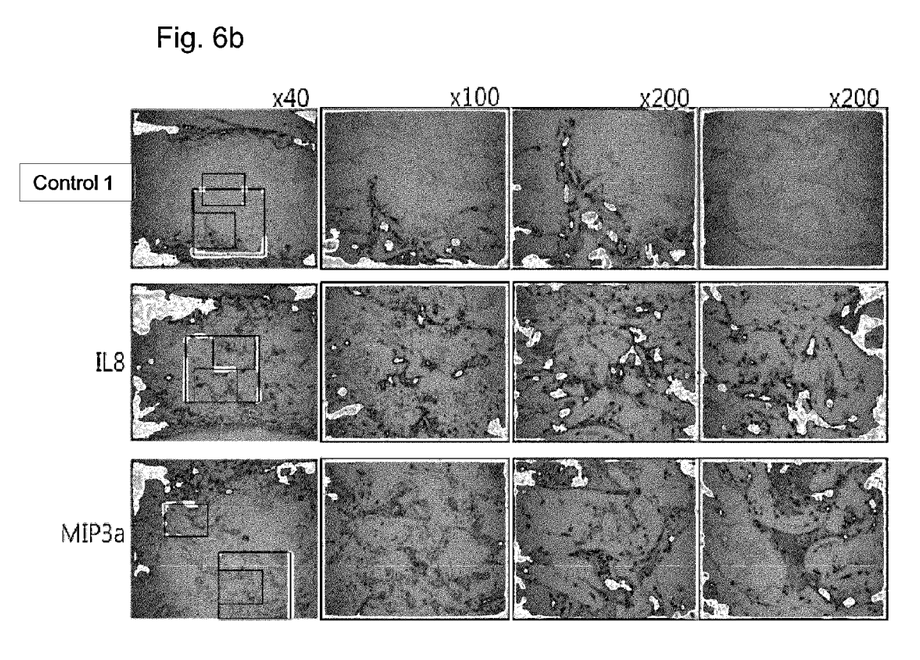
FIG. 6b represents images of pathological analysis.

As a result of visual observation, the IL8- and MIP-3α containing scaffolds were more compactly fused with the surrounding tissues, and there were more blood vessels in the scaffolds compared with the PBS-containing control scaffolds (FIG. 6a). As a result of H&E staining, blood vessel formation was occasionally seen on the edge of the PBS-containing scaffolds, and there was no cell infiltration or blood vessel formation on the inner part of the PBS-containing scaffolds. Vascular infiltration was found in both the edge and the interior of IL-8- or MIP-3α-soaked scaffolds; a large number of fibroblastic cells were found surrounding blood vessels and inside the pores of the scaffolds. Additionally, active ECM formation by these fibroblastic cells, potentially recruited MSCs, was found in the interior of the scaffolds containing chemokines. There were only a few inflammatory cells such as macrophages in the PBS, IL-8- and MIP-3α-containing scaffolds, which were no significant difference between them. Therefore, no significant inflammatory reaction was observed in any groups (FIG. 6b).

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

References

1. Hunter W. Of the structure and disease of articulating cartilages. 1743. Philos Trans R SocLond 1995; 42b:514-21.
2. Buckwalter J A, Mankin H J. Articular cartilage repair and transplantation. Arthritis Rheum 1998; 41:1331-42.
3. Pridie K. A method of resurfacing osteoarthritis knee joints. J Bone Joint Surg Br 1959; 41: 6189.
4. Steadman J R, Rodkey W G, Briggs K K, Rodrigo J J. The microfracture technic in the management of complete cartilage defects in the knee joint. Orthopade 1999; 28:26-32
5. Brittberg M, Lindahl A, Nilsson A, Ohlsson C, Isaksson O, Peterson L. Treatment of deep cartilage defects in the knee with autologous chondrocyte transplantation. N Engl J Med 1994; 331:889-95.
6. Pelttari K, Lorenz H, Boeuf S, Templin M F, Bischel O, Goetzke K, et al. Secretion of matrix metalloproteinase 3 by expanded articular chondrocytes as a predictor of ectopic cartilage formation capacity in vivo. Arthritis Rheum 2008; 58:467-74.
7. Kessler M W, Ackerman G, Dines J S, Grande D. Emerging technologies and fourth generation issues in cartilage repair. Sports Med Arthrosc 2008; 16:246-54.
8. DeLise A M, Fischer L, Tuan R S. Cellular interactions and signaling in cartilage development. Osteoarthritis Cartilage 2000; 8:309-34.
9. Dickhut A, Gottwald E, Steck E, Heisel C, Richter W. Chondrogenesis of mesenchymal stem cells in gel-like biomaterials in vitro and in vivo. Front Biosci 2008; 13:4517-28.
10. Steck E, Fischer J, Lorenz H, Gotterbarm T, Jung M, Richter W. Mesenchymal stem cell differentiation in an experimental cartilage defect: restriction of hypertrophy to bone-close neocartilage. Stem Cells Dev 2009; 18:969-78.
11. Zhao L R, Duan W M, Reyes M, Keene C D, Verfallie C M, Low W C. Human bone marrow stem cells exhibit neural phenotypes and ameliorate neurological deficits after grafting into the ischemic brain of rats. ExpNeurol 2002; 174:11-20.
12. Jin H K, Carter J E, Huntley G W, Schuchman E H. Intracerebral transplantation of mesenchymal stem cells into acid sphingomyelinase deficient mice delays the onset of neurological abnormalities and extends their life span. J Clin Invest 2002; 109:1183-91.
13. Turgeman G, Pittman D D, Muller R, Kurkalli B G, Zhou S, Pelled G, et al. Engineered human mesenchymal stem cells: a novel platform for skeletal cell mediated gene therapy. J Gene Med 2001; 3:240-51.
14. Lapidot T, Dar A, Kollet O. How do stem cells find their way home? Blood 2005; 106:1901-10.
15. Frenette P S, Subbarao S, Mazo I B, vonAndrian U H, Wagner D D. Endothelial selectins and vascular cell adhesion molecule-1 promote hematopoietic progenitor homing to bone marrow. ProcNatlAcadSci USA 1998; 95:14423-8.
16. Papayannopoulou T, Priestley G V, Nakamoto B, Zafiropoulos V, Scott L M. Molecular pathways in bone marrow homing: dominant role of a(4)b(1) over b(2)-integrins and selectins. Blood 2001; 98:2403-11.
17. Lapidot T, Kollet O. The essential roles of the chemokine SDF-1 and its receptor CXCR4 in human stem cell homing and repopulation of transplanted immune-deficient NOD/SCID and NOD/SCID/B2m (null) mice. Leukemia 2002; 16:1992-2003.
18. Baggiolini M. Chemokines in pathology and medicine. J Intern Med 2001; 250:91-104.
19. Luster A D. Chemokineschemotactic cytokines that mediate inflammation. N Engl J Med 1998; 338:436-45.
20. Rollins B J. Chemokines. Blood 1997; 90:909-28.
21. Richard H. Chemokine receptors. Cytokine and Growth Factor Reviews 2001; 12; 313-35.
22. Ponte A L, Marais E, Gallay N, LangonnA, Delorme B, H O, et al. The in vitro migration capacity of human bone marrow mesenchymal stem cells: comparison of chemokine and growth factor chemotactic activities. Stem Cells 2007; 25:1737-45.
23. Sasaki M, Abe R, Fujita Y, Ando S, Inokuma D, Shimizu H. Mesenchymal stem cells are recruited into wounded skin and contribute to wound repair by transdifferentiation into multiple skin cell type. J Immunol 2008; 15:2581-7.

What is claimed is:

1. A method for inducing in vivo migration of a therapeutic cell to a damaged tissue, comprising:
   administering at least one chemotactic factor or a combination of chemotactic factors selected from the group consisting of (i) MIP (Macrophage Inflammatory Protein)-3α; and (ii) IL-8 and MIP-3α to a damaged tissue,
   wherein the damaged tissue is a bone tissue, an articular tissue, or a skin tissue,
   wherein the therapeutic cell is a stem cell or a keratinocyte, and
   wherein IL-8 and MIP-3α induce chemotaxis of the therapeutic cell.

2. The method according to claim 1, wherein the chemotactic factor is comprised within a biodegradable scaffold and the chemotactic factor is administered to the damaged tissue by implanting the biodegradable scaffold into the damaged tissue, and wherein the biodegradable scaffold is selected from the group consisting of a PLGA (poly(lactic-co-glycolic acid)), a PLA (polylactic acid), a PGA (polyglycolic acid), a PCL (poly-ε-caprolactone), a PAA (poly(amino acid)), a poly(anhydride), a polyorthoesther, a collagen gel, a hydrogel, a polyvinyl alcohol sponge, a gelatin, a polysaccharide, a polyphosphazene, a polyacrylate, a polyethylene oxide-propylene glycol block copolymer and mixtures thereof.

3. The method according to claim 1, wherein the articular tissue is hip joint, shoulder, knee, ankle, wrist, elbow, tarsal bone, ulna, vertebra, wristbone, metacarpus or temprormandibular joint.

4. The method according to claim 1, wherein the skin tissue is epidermis, hypodermis or subcutaneous tissue.

5. The method according to claim 1, wherein the stem cell is an autologous stem cell.

6. The method according to claim 1, wherein the stem cell is a mesenchymal stem cell (MSCs) or an ectodermal stem cell.

7. The method according to claim 1, wherein the method is applied to a mammal.

8. A method for treating a damaged tissue, comprising:
   administering at least one chemotactic factor or a combination of chemotactic factors selected from the group consisting of (i) MIP (Macrophage Inflammatory Protein)-3α; and (ii) IL (interleukin)-8 and MIP (Macrophage Inflammatory Protein)-3α to a damaged tissue of a subject in need thereof,
   wherein the damaged tissue is a bone tissue, an articular tissue, or a skin tissue,
   wherein the chemotactic factor is comprised within a biodegradable scaffold and the chemotactic factor is administered to the damaged tissue by implanting the biodegradable scaffold into the damaged tissue,
   wherein the biodegradable scaffold implanted induces in vivo migration of a therapeutic cell to the damaged tissue and the therapeutic cell is a stem cell or a keratinocyte, and
   wherein IL-8 and MIP-3α induce chemotaxis of the therapeutic cell.

9. The method according to claim 8, wherein the biodegradable scaffold is selected from the group consisting of a PLGA (poly(lactic-co-glycolic acid)), a PLA (polylactic acid), a PGA (polyglycolic acid), a PCL (poly-ε-caprolactone), a PAA (poly(amino acid)), a poly(anhydride), a polyorthoesther, a collagen gel, a hydrogel, a polyvinyl alcohol sponge, a gelatin, a polysaccharide, a polyphosphazene, a polyacrylate, a polyethylene oxide-propylene glycol block copolymer and mixtures thereof.

10. The method according to claim 8, wherein the articular tissue is hip joint, shoulder, knee, ankle, wrist, elbow, tarsal bone, ulna, vertebra, wristbone, metacarpus or temprormandibular joint.

11. The method according to claim 8, wherein the skin tissue is epidermis, hypodermis or subcutaneous tissue.

12. The method according to claim 8, wherein the stem cell is an autologous stem cell.

13. The method according to claim 8 wherein the stem cell is a mesenchymal stem cell (MSCs) or an ectodermal stem cell.

14. The method according to claim 8, wherein the subject is a mammal.

* * * * *

SEQUENCE LISTING

<160> NUMBER OF SEQ ID NOS: 2

<210> SEQ ID NO 1
<211> LENGTH: 70
<212> TYPE: PRT
<213> ORGANISM: Artificial Sequence
<220> FEATURE:
<223> OTHER INFORMATION: MIP-3a

<400> SEQUENCE: 1

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

-continued

```
Lys Lys Val Lys Asn Met
 65                  70

<210> SEQ ID NO 2
<211> LENGTH: 72
<212> TYPE: PRT
<213> ORGANISM: Artificial Sequence
<220> FEATURE:
<223> OTHER INFORMATION: IL-8

<400> SEQUENCE: 2

Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
             20                  25                  30

His Cys Ala Asn Thr Glu Ile Ile Val Lys Leu Ser Asp Gly Arg Glu
         35                  40                  45

Leu Cys Leu Asp Pro Lys Glu Asn Trp Val Gln Arg Val Val Glu Lys
     50                  55                  60

Phe Leu Lys Arg Ala Glu Asn Ser
 65                  70
```